United States Patent [19]

Turley et al.

[11] 3,989,773

[45] Nov. 2, 1976

[54] METHOD FOR DECOLORIZING PHOSPHATE POLYESTERS

[75] Inventors: Richard J. Turley, Orange; Alexandre Ozolins, New Haven; Robert B. Lauder, Fairfield, all of Conn.

[73] Assignee: Olin Corporation, New Haven, Conn.

[22] Filed: July 24, 1975

[21] Appl. No.: 598,614

[52] U.S. Cl. .............................. 260/989; 260/928; 260/930
[51] Int. Cl.² .................................. C07F 9/09
[58] Field of Search .................................. 260/989

[56] References Cited
UNITED STATES PATENTS
2,844,620    7/1958    Nebrera .............................. 260/989

OTHER PUBLICATIONS
Kirk–Othmer, "Encyclopedia of Chemical Technology," vol. 5, 1964, p. 11.

*Primary Examiner*—Anton H. Sutto
*Attorney, Agent, or Firm*—F. A. Iskander; T. P. O'Day

[57] ABSTRACT

Selected bleaching agents are used to decolorize off-color phosphate polyesters.

13 Claims, No Drawings

METHOD FOR DECOLORIZING PHOSPHATE POLYESTERS

This invention relates to a method for decolorizing phosphate polyesters.

Various phosphate polyesters have been known and used in a number of industrial applications. For example, by virtue of their relatively high phosphorus content, these polyesters have been extensively used as additives for reducing the combustibility of synthetic plastics. For this application, certain halogenated phosphate polyesters have been found to be particularly effective. See for example U.S. Pat. Nos. 3,707,586 and 3,157,613.

However, an unexpected problem has recently been identified in connection with the production and utilization of these phosphate polyesters. Specifically, it has been found that due to yet undetermined factors, they often become discolored. Thus instead of the characteristic light color, quite often they acquire a pronounced brownish color which varies in intensity from one production lot to another. This discoloration phenomenon is highly objectionable in those additive or reactive applications wherein a final product having a uniform color is required. Furthermore, from a purely marketing standpoint, the off-color product is undesirable because, even though it may be equivalent in all other chemical and physical properties to the undiscolored material, it often fails to gain customer acceptance and thus becomes unsalable. The net result is that due to discoloration, substantial quantities of industrially-manufactured phosphate polyesters whould have to be discarded or wasted as being unusable and/or unmarketable.

Now a simple method has been found for decolorizing off-color phosphate polyesters. According to the invention, this method comprises treating or contacting the off-color polyester with selected bleaching agents, namely, halogen or a hypohalous acid solution. These bleaching agents have been found to be particularly effective in this type of application to the exclusion of several other prior art bleaching agents. As such, their use according to the invention provides a practically and economically attractive expedient for resolving the discoloration problem.

Generally speaking, it is contemplated that the method of the invention can be used in decolorizing any off-color material having 2 or more phosphate groups. It is particularly useful, however, in decolorizing those halogenated phosphate polyesters which are represented by the formula $$RX_a[OP(OR')_2]_n \quad I$$

wherein

R is an aliphatic hydrocarbon radical having 1–8 carbon atoms, or an aromatic hydrocarbon radical having 6–14 carbon atoms, X is a halogen selected from chlorine, bromine and a mixture thereof, $a$ is an integer of 0–4, $n$ is an integer of 2–6, and each R' is independently a haloalkyl radical having 1–8 carbon atoms, the halogen in this radical being chlorine, bromine or a mixture thereof. These polyesters and their preparation are described in U.S. Pat. No. 3,707,586, which issued to R. J. Turley on Dec. 26, 1972. The entire disclosure of this patent is incorporated herein by reference.

Preferred polyesters for treatment according to the invention are those of formula I above wherein R represents an aliphatic hydrocarbon radical having 1–8 carbon atoms, all the radicals represented by R' are identical and $n$ is 2. Furthermore, it is generally more preferred to treat those polyesters of formula I wherein all the halogens are chlorine, i.e., X is chlorine and all the radicals represented by R' are chloroalkyl.

Illustrative of the preferred polyesters are the following:

tetrakis(2-chloroethyl)ethylene diphosphate
tetrakis(2-chloroisopropyl)ethylene disphosphate
tetrakis(2-chloroethyl)p-phenylene diphosphate
tetrakis(2-chloroethyl)m-phenylene diphosphate
tetrakis(2-chloroethyl)tetrachloro-p-phenylene diphosphate
tetrakis(2-bromoethyl)ethylene diphosphate
tetrakis(2-chloroethyl)-2-butene-1,4-diphosphate
tetrakis(2-chloroethyl)-2,3-dibromobutylene-1,4-diphosphate
tetrakis(2-bromoisopropyl)ethylene diphosphate
2,2-bis(chloromethyl)-1,3-propylene-bis [bis(2-chloroethyl) phosphate]
2,2-bis(chloromethyl)-1,3-propylene-bis [bis(2-bromoethyl) phosphate]
2,2-bis(chloromethyl)-1,3-propylene-bis [bis(2-chloropropyl) phosphate]
2,2-bis(bromomethyl)-1,3-propylene-bis [bis(2-bromoethyl) phosphate] 2,2-bis(bromoethyl)-1,3-propylene-bis[bis(2-chloroethyl) phosphate]
tetrakis(2,3-dichloropropyl)ethylene diphosphate
tetrakis(2,3-dibromopropyl)ethylene diphosphate
tetrakis(2-bromoethyl)-2-butene-1,4-diphosphate A particularly preferred group of phosphate polyesters which are amenable to treatment by the method of the invention are those represented by formula II as follows:

$$\begin{matrix} R'O & O & & O & OR' \\ & \diagdown \| & & \| \diagup & \\ & P-O-R-O-P & \\ & \diagup & & \diagdown & \\ R'O & & & OR' \end{matrix} \quad II$$

wherein

R' is a chloroalkyl radical having 1–8, and more preferably 1–4, carbon atoms, and R is an alkylene radical having 1–8, and more preferably 1–4, carbon atoms.

Compounds which are illustrative of those represented by formula II include tetrakis(2-chloroethyl)ethylene diphosphate, tetrakis(2-chloroisopropyl)ethylene diphosphate, and tetrakis(2-chloroethyl)-2-butene-1,4-diphosphate.

Decolorization of off-color phosphate polyesters is achieved by treating them with a halogen or with a hypohalous acid solution. The selection of these particular bleaching agents is a critical feature of the invention; for it has been found that several other prior art bleaching agents exhibit little or no effect in this application. Such has been found to be the case, for example, with the well-known bleaching agents chlorine dioxide, sodium chlorite and hydrogen peroxide.

The halogen which is used as a decolorizing agent in the method of the invention is chlorine or bromine, chlorine being preferred for economic reasons. In utilizing the halogen, this can be bubbled into the phosphate polyester as a gas; or alternatively, and in accordance with a preferred embodiment of the invention, the halogen may be preparatorily dissolved in an organic solvent, the solution being thereafter added to, and mixed with, the phosphate polyester. Utilizing the latter practice, any organic liquid which is not reactive with the halogen and the phosphate polyester but which is a solvent for the halogen may be used. This includes any aromatic and aliphatic solvent provided it meets these two criteria. However, in practice it is preferred to employ such readily available solvents as carbon tetrachloride, chloroform, ethylene dichloride and the like, ethylene dichloride being especially preferred. Along with their commercial availability and relative low cost, such solvents can be easily separated from the phosphate polyester by a simple stripping operation after the decolorization treatment is completed.

The other bleaching agent which has been found effective in decolorizing off-color phosphate polyesters is a hypohalous acid solution, the halogen therein being chlorine or bromine. Here again, however, for reasons of economy and commercially availability it is preferred to employ a hypochlorus acid solution.

As is well known in the art, hypohalous acid solutions can be prepared from a variety of materials which are characterized by having free available halogen. A common characteristic of these materials is that when dissolved in water, they form hypohalous acid solutions. For a detailed description of the chemistry of free available halogen-containing materials, see J. S. Sconce, *Chlorine, Its Manufacture, Properties And Uses*, Reinhold Publishing Corporation, New York (1962).

In preparing the hypohalous acid solution, any material which contains free available halogen, and which therefore forms hypohalous acid in water, may be employed. In addition to halogen gas as such, this includes various organic as well as inorganic materials. Illustrative inorganic materials include for example the alkali metal (e.g., Na, K, Li, Rb, Cs) hypohalites, such as sodium hypochlorite, sodium hypobromite, and potassium hypochlorite, and the alkaline earth metal (e.g., Ca, Mg, Ba, Sr) hypohalites such as calcium hypochlorite, calcium hypobromite and dibasic magnesium hypochlorite. And illustrative organic materials include the haloisocyanuric acids, such as di- and trichloroisocyanuric acid, salts of these acids, such as sodium dichloroisocyanurate, and the alkyl hypohalites such as t-butyl hypochlorite.

The more preferred free available halogen-containing materials for use in preparing the hypohalous acid solution are chlorine, sodium hypochlorite, calcium hypochlorite, dichloroisocyanuric acid, trichloroisocyanuric acid, and sodium dichloroisocyanurate, the sodium and calcium hypochlorites being most preferred.

It should be noted that the hypohalous acid solution may be prepared or brought into contact with the phosphate polyester using any convenient procedural techniques. For example, it may be prepared by simply dissolving the free available halogen-containing material in water, the solution being thereafter added to the phosphate polyester. Alternatively, the water and free available halogen-containing material may be added separately to the phosphate polyester, the hypohalous acid solution being formed in situ thereafter.

It should further be noted that the hypohalous acid solutions which are used according to the invention need not be limited to aqueous solutions. Thus where practicable, non-aqueous solutions may be employed. It is generally preferred, however, to employ aqueous solutions, it being understood that such solution may contain an additional non-aqueous solvent. Thus any such solution is encompassed by the term "aqueous solution" as used in the specification and claims herein.

In practicing the method of the invention, the proportion and/or concentration of bleaching agent which is used is not critical. Whatever proportion and/or concentration may be suitably employed which is effective in achieving the required degree of discolorization in the particular phosphate polyester. Thus the term "effective decolorizing amount" as used in the specification and claims herein refers to any such suitable proportion and/or concentration.

To illustrate, the halogen gas, when used as is, may be employed in a proportion ranging from about 0.001 to about 20, and preferably about 0.1–10, parts per every 100 parts by weight of the phosphate polyester. Where the halogen is supplied in the form of a solution thereof in an organic solvent, the solution concentration may illustratively range from about 0.01 percent by weight all the way up to saturation, with a preferred concentration range of about 0.1–10 percent by weight; and depending on its concentration, this solution may be used in a proportion ranging for example from about 5 to about 500, and preferably about 10–300, parts per every 100 parts by weight of the phosphate polyester.

Turning to the hypohalite solution, illustrative concentrations of free available halogen therein may range from about 1 to about 300,000 parts per million parts by weight. A preferred range is about 50–100,000 parts of free available halogen per million parts by weight. Furthermore, depending on its concentration, the hypohalite solution may be employed in a proportion ranging for example from about 5 to about 500, and preferably about 10–300, parts per every 100 parts by weight of the phosphate polyester.

In practicing the invention, the bleaching agent may be added and mixed with the polyester for such length of time and using such effective decolorizing amounts as are necessary to eliminate the discoloration or reduce it to an acceptable level. Thereafter, the bleaching agent is removed using conventional techniques such as by repeated water washings. Any acidity that may be present may be neutralized by an initial wash with a dilute aqueous basic solution; and if an organic solvent is present, this is finally removed by stripping.

The decolorizing method of the invention may be conveniently incorporated, as an improvement, into the over-all process for preparing phosphate polyesters. Consider for example the process for preparing tetrakis(2-chloroethyl)ethylene diphosphate as described in U.S. Pat. No. 3,803,272 which issued Apr. 9, 1974 to Pivawer et al. In that process, the tetrakis(2-chloroethyl)ethylene diphosphate is prepared in the presence of a solvent, e.g., ethylene dichloride, which is subsequently removed. Pursuant to one embodiment of the invention, before the solvent is removed, halogen is added either in gaseous form or preferably as a solution thereof in an organic solvent. This solvent may conveniently be the same solvent, e.g., ethylene dichloride, which is used according to the Pivawer et al. patent. After adequate mixing, the combined solvent can then be removed in a single step. Alternatively, and in accordance with another embodiment of the invention, decolorization of the tetrakis(2-chloroethyl)ethylene diphosphate may be carried out as an added step after solvent removal. Using this practice, the bleaching agent and solvent, if such is used, are then removed in the final stages of product purification and recovery.

The following examples are provided to illustrate the invention. In these examples, all parts and percentages are by weight unless otherwise specified.

EXAMPLE 1

A 50-gram sample of an off-color production lot of tetrakis(2-chloroethyl) ethylene diphosphate was placed in a test tube and checked for color using a standard Gardner color scale. As compared with another undiscolored production lot which had a Gardner color of 1–2, the sample had a Gardner color of 6.

To decolorize it, the sample was washed successively with two 10-mls. portions of a 5.25 percent aqueous solution of sodium hypochlorite having a pH of 7. As a result of this treatment, a visible reduction in color intensity was observed. The sample was then neutralized by washing with a dilute aqueous solution of sodium metabisulfite followed by four repeated washings with water. Thereafter the color of the sample was tested again and the test gave a Gardner color of 1–2.

COMPARISONS 1–3

Three comparisons, identified as C-1, C-2, and C-3, were carried out to test the effectiveness of other prior art bleaching agents in decolorizing samples tetrakis(2-chloroethyl)ethylene diphosphate. These samples were taken from the same off-color production lot used in Example 1.

In comparison C-1, a 50-gram sample of the diphosphate was mixed for 20 minutes with 1.5 grams of a 30% aqueous solution of hydrogen peroxide having a pH of 11. As a result of this treatment, no change in color was observed.

In comparison C-2, another 50-gram sample of the diphosphate was treated with an aqueous solution of chlorine dioxide at a pH of 7. Again no decolorizing effect was noted.

In comparison C-3, a third 50-gram sample of the diphosphate was treated for 10 minutes with an aqueous solution of sodium chlorite having a pH of 3. The sodium chlorite solution had been prepared by mixing 1.5 grams of 80 percent solid sodium chlorite with 30 mls. of water. After work-up, the sample had a Gardner color of 4–5.

The above-described comparisons are provided to demonstrate that prior art bleaching agents, other than those prescribed according to the invention, have little or no effect as decolorizing agents for phosphate polyesters.

EXAMPLE 2

Twenty-five grams of the off-color tetrakis(2-chloroethyl) ethylene diphosphate used in Example 1 were dissolved in 25 mls. of ethylene dichloride which contained a small but undetermined amount of water. This solution was added to and thoroughly mixed with a chlorine solution prepared by dissolving 35 mgs. of chlorine in 25 mls. of ethylene dichloride. Thereafter the mixture was washed successively with a dilute aqueous solution of sodium hydroxide and then with water. After stripping off the ethylene dichloride, the remaining diphosphate had a Gardner color of 1–2.

EXAMPLE 3

The general procedure of the preceding examples was used to test and confirm the utility, as a decolorizing agent, in an aqueous solution of sodium dichloroisocyanurate dihydrate.

What is claimed is:

1. A method for decolorizing an off-color phosphate polyester represented by the formula

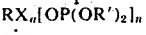

wherein
R is an aliphatic hydrocarbon radical having 1–8 carbon atoms, or an aromatic hydrocarbon radical having 6–14 carbon atoms,
X is a halogen selected from chlorine, bromine and a mixture thereof,
$a$ is an integer of 0–4,
$n$ is an integer of 2–6, and
each R' is independently a haloalkyl radical having 1–8 carbon atoms in which the halogen is chlorine, bromine or a mixture thereof, which method comprises contacting said phosphate polyester with an effective decolorizing amount of a bleaching agent selected from the group consisting of chlorine, bromine, an aqueous hypochlorite solution and an aqueous hypobromite solution.

2. The method of claim 1 wherein said bleaching agent is chlorine or a hypochlorite solution.

3. The method of claim 2 wherein said phosphate polyester is tetrakis(2-chloroethyl)ethylene diphosphate.

4. The method of claim 2 wherein, as applied to said formula, R represents an aliphatic hydrocarbon radical having 1–8 carbon atoms, $n$ is 2 and all the radicals represented by R' are identical.

5. The method of claim 4 wherein, as applied to said formula, X is chlorine and R' is chloroalkyl.

6. The method of claim 5 wherein said phosphate polyester is represented by the formula

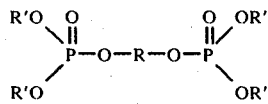

wherein
R' represents a chloroalkyl radical having 1–4 carbon atoms and
R represents an alkylene radical having 1–4 carbon atoms.

7. The method of claim 6 wherein said bleaching agent is chlorine.

8. The method of claim 7 wherein said chlorine is supplied as a solution thereof in an organic solvent.

9. The method of claim 8 wherein said solvent is ethylene dichloride.

10. The method of claim 9 wherein said phosphate polyester is tetrakis(2-chloroethyl)ethylene diphosphate.

11. The process of claim 6 wherein said hypochlorite solution is provided by dissolving in water a free available chlorine-containing material selected from the group consisting of chlorine, sodium hypochlorite, calcium hypochlorite, dichloroisocyanuric acid, trichloroisocyanuric acid, and sodium dichloroisocyanurate.

12. The process of claim 11 wherein said free available chlorine-containing material is sodium hypochlorite or calcium hypochlorite.

13. The method of claim 12 wherein said phosphate polyester is tetrakis(2-chloroethyl)ethylene diphosphate.

* * * * *

UNITED STATES PATENT OFFICE
CERTIFICATE OF CORRECTION

Patent No. 3,989,773     Dated November 2, 1976

Inventor(s) Richard J. Turley, Alexandre Ozolins and Robert B. Lauder

It is certified that error appears in the above-identified patent and that said Letters Patent are hereby corrected as shown below:

Column 1, line 54, change the formula "$RX_a[OP(OR')_2]_n$" to read $$--RX_a[O\overset{\overset{O}{\|}}{P}(OR')_2]_n--.$$

Column 6, line 9, change the formula "$RX_a[OP(OR')_2]_n$" to read $$--RX_a[O\overset{\overset{O}{\|}}{P}(OR')_2]_n--.$$

Signed and Sealed this

Eighth Day of March 1977

[SEAL]

Attest:

RUTH C. MASON
*Attesting Officer*

C. MARSHALL DANN
*Commissioner of Patents and Trademarks*